(12) United States Patent
Ohno et al.

(10) Patent No.: US 7,799,959 B2
(45) Date of Patent: Sep. 21, 2010

(54) PROCESS FOR PRODUCING 1,2,3,4-TETRACHLOROHEXAFLUOROBUTANE

(75) Inventors: Hiromoto Ohno, Kawasaki (JP); Toshio Ohi, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 12/298,843

(22) PCT Filed: Apr. 25, 2007

(86) PCT No.: PCT/JP2007/058988

§ 371 (c)(1),
(2), (4) Date: Jan. 30, 2009

(87) PCT Pub. No.: WO2007/125975

PCT Pub. Date: Nov. 8, 2007

(65) Prior Publication Data

US 2009/0216054 A1 Aug. 27, 2009

(30) Foreign Application Priority Data

Apr. 28, 2006 (JP) .............................. 2006-126976

(51) Int. Cl.
*C07C 17/00* (2006.01)
(52) U.S. Cl. ..................................................... 570/161
(58) Field of Classification Search .................. 570/161
See application file for complete search history.

(56) References Cited

U.S. PATENT DOCUMENTS 2,688,182 A 9/1954 Dorst

FOREIGN PATENT DOCUMENTS

EP 0 270 956 B1 1/1991
JP 62-26240 A 4/1987

OTHER PUBLICATIONS

Akopyan et al., Butadiene chlorination in a solvent medium in the presence of catalysts, Armyanskii Khimicheskii Zhurnal (1979), 32(11), 890-5.*
English machine translation of JP 2006-342059 (2006).*
Adcock, James L., et al., "Aerosol Direct Fluorination of C1 and C2 Chlorocarbons," Ind. Eng. Chem. Res., 1989, pp. 1547-1549, vol. 28, American Chemical Society.
Haszeldine, R.N., "The Synthesis of Hexaflurobutadiene," J. Chemical Society, 1952, pp. 4423-4431.
Lo, Elizabeth S., "Reaction of Perfluoroalkyl Halides with Grignard Reagents," J. Org. Chem., 1971, pp. 364-366, vol. 36, No. 2.

* cited by examiner

*Primary Examiner*—Jafar Parsa
(74) *Attorney, Agent, or Firm*—Sughrue Mion, PLLC

(57) ABSTRACT

Disclosed is a process for producing 1,2,3,4-tetrachlorohexafluorobutane safely in a high yield in the industrial viewpoint and at low cost in the economical viewpoint. Specifically disclosed is a process for producing 1,2,3,4-tetrachlorohexafluorobutane which process comprises: (1) a step of chlorinating 1,3-butadiene, thereby preparing a mixture containing 1,2,3,4-tetrachlorobutane, and (2) a step of allowing the 1,2,3,4-tetrachlorobutane prepared in the step (1) to react with a fluorine gas in the presence of a diluting gas in a gas phase, thereby preparing a mixture containing 1,2,3,4-tetrachlorohexafluorobutane.

14 Claims, No Drawings

PROCESS FOR PRODUCING 1,2,3,4-TETRACHLOROHEXAFLUOROBUTANE

TECHNICAL FIELD

The present invention relates to a process for producing 1,2,3,4-tetrachlorohexafluorobutane. More specifically, it relates to a process for producing 1,2,3,4-tetrachlorohexafluorobutane which is useful as a precursor in synthesizing hexafluoro-1,3-butadiene of use as an etching gas for semiconductors.

TECHNICAL BACKGROUND 1,2,3,4-tetrachlorohexafluorobutane is a useful compound used as a raw material for synthesizing hexafluoro-1,3-butadiene which is a fine etching gas for semiconductors.

As a method of synthesizing a halogen compound having four carbon atoms, the following methods are known conventionally.

(1) Non-patent document 1 discloses that ICl is added to a raw material $CClF=CF_2$ to prepare $CClF_2-CClFI$, and then $CClF_2-CClF-CClF-CClF_2$ is synthesized in the presence of Hg by photo-reaction.

(2) Patent document 1 discloses that a raw material $CClF=CF_2$ is reacted at 550° C. to prepare $CF_2=CF-CClF-CClF_2$, and then it is subjected to chlorination or bromination to prepare $CClF_2-CClF-CClF-CClF_2$ or $CBrF_2-CBrF-CClF-CClF_2$, respectively.

(3) Patent document 1, Patent document 2 and Non-Patent document 2 disclose that a raw material $CF_2=CF_2$ is subjected to iodine addition reaction or bromine addition reaction to prepare $XCF_2-CF_2X$ (X=I or Br) and then it is subjected to telomerization reaction to synthesize $XCF_2-CF_2-CF_2-CF_2X$.

Patent document 1: Specification in U.S. Pat. No. 2,668,182

Patent document 2: Publication EP-B-0,270,956

Patent document 3: JP-A-62 (1987)-26240

Non-patent document 1: R. N. Haszeldine, J. Chem. Soc., 4423 (1952)

Non-patent document 2: J E. S. Elizabath, J. Org. Chem., 36 (1971)364

DISCLOSURE OF THE INVENTION

Object of the Invention

The method (1), however, has a problem in industrial production such that it is difficult to obtain $CClF=CF_2$ industrially, and $CClF=CF_2$ and ICl are expensive. The method (2) also has a problem in industrial production such that the raw material is expensive, the reaction yield is low, and the amount of by-products is large. Furthermore, the method (3) also has a problem in industrial production that the raw material, and iodine and bromine to be added are expensive.

In view of the situation as described above, it is an object of the invention to provide a process for producing 1,2,3,4-tetrachlorohexafluorobutane, which is useful as a precursor in producing hexafluoro-1,3-butadiene which is used suitably as an etching gas for semiconductors, safely in the production viewpoint and at low cost in the economical viewpoint.

Means for Solving the Problems

The present inventors have been earnestly studied in order to solve the problems as described above, and found that 1,2,3,4-tetrachlorohexafluorobutane can be prepared safely in a high yield in the industrial viewpoint and at low cost in the economical viewpoint by a step of chlorinating 1,3-butadiene, thereby preparing 1,2,3,4-tetrachlorobutane, and a step of allowing the resulting 1,2,3,4-tetrachlorobutane to react with a fluorine gas in a gas phase thereby preparing 1,2,3,4-tetrachlorohexafluorobutane. Thus, the present invention has been accomplished.

Effect of the Invention

The present invention can provide a process for producing 1,2,3,4-tetrachlorohexafluorobutane safely in the industrial viewpoint and usefully in the economical viewpoint, and the process comprises a step of chlorinating 1,3-butadiene, thereby preparing 1,2,3,4-tetrachlorobutane, and a step of allowing the resulting 1,2,3,4-tetrachlorobutane to react with a fluorine gas in a gas phase, thereby preparing 1,2,3,4-tetrachlorohexafluorobutane.

BEST EMBODIMENT FOR CARRYING OUT THE INVENTION

The preferred embodiments of the present invention will be described in detail, but the present invention is not limited by these embodiments. In the present invention, various modifications can be made within the concept and achievement of the present invention.

The production process of the present invention comprises (1) a step of chlorinating 1,3-butadiene, thereby preparing a mixture containing 1,2,3,4-tetrachlorobutane, and (2) a step of allowing the resulting 1,2,3,4-tetrachlorobutane prepared in the step (1) to react with a fluorine gas in the presence of a diluting gas in a gas phase thereby preparing a mixture containing 1,2,3,4-tetrachlorohexafluorobutane.

In the step (1), 1,3-butadiene is chlorinated to prepare a mixture containing 1,2,3,4-tetrachlorobutane. As described in the technical background, a compound having four carbon atoms bonded to a bromine atom or an iodine atom is expensive and has high corrosive properties. Therefore, the step (1) is sometimes at high cost in the economical viewpoint.

1,2,3,4-Tetrachlorobutane is produced, as a by-product, in a step of industrially producing a chloroprene rubber in the following formulas that the formula (1) indicates an objective reaction and the formula (2) indicates a by-product reaction, and it is made harmless by burning treatment or the like together with other by-product chlorine compounds in the present condition.

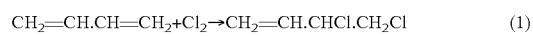  (1)

  (2)

Accordingly, from the viewpoint of depressing the cost by the use of the by-product, the step (1) preferably comprises chlorinating 1,3-butadiene, thereby preparing a mixture containing 1,2,3,4-tetrachlorobutane and 3,4-dichlorobutene-1. Furthermore, the 1,2,3,4-tetrachlorobutane is preferably a by-product of the chlorination.

In the production step of the chloroprene rubber, 1,3-butadiene is subjected to chlorination reaction and isomerization and thereafter, objective 3,4-dichlorobutene-1 and other by-product chlorine compounds are separated by distillation of the product. The other by-product chlorine compounds can be recycled, but they are made harmless by burning or the like in the present condition, as described above. In the production of the chloroprene rubber, chloroprene is produced from the objective 3,4-dichlorobutene-1 by dehydrochlorination.

In the production process of the present invention, it is preferred that the by-product chlorine compounds be separated and purified by at least one distillation column, and thereby 1,2,3,4-tetrachlorobutane be recovered and then used in the step (2). That is to say, the production process of the present invention preferably comprises, further, (3) a step of separating 1,2,3,4-tetrachlorobutane from the mixture containing 1,2,3,4-tetrachlorobutane prepared in the step (1), and the step (2) preferably comprises allowing the 1,2,3,4-tetrachlorobutane prepared in the step (3) to react with a fluorine gas, thereby preparing a mixture containing 1,2,3,4-tetrachlorohexafluorobutane.

In the separation and purification, further, 1,2,3,4-tetrachlorobutane having a purity of preferably 95 mol % or higher, more preferably 98 mol % or higher is desirably recovered and used in the step (2). When the purity is lower than 95 mol %, a by-product is produced in the step (2) (direct fluorination process) thereby sometimes causing complicate separation and purification or economical problems such as an increase in cost.

The production process of the present invention preferably comprises, further, (4) a step of separating 3,4-dichlorobutene-1 from the mixture containing 1,2,3,4-tetrachlorobutane prepared in the step (1), and (5) a step of chlorinating the 3,4 dichlorobutene-1 prepared in the step (4), thereby preparing 1,2,3,4-tetrachlorobutane. The step (2) preferably comprises allowing the 1,2,3,4-tetrachlorobutane prepared in the step (5) to react with a fluorine gas, thereby preparing a mixture containing 1,2,3,4-tetrachlorohexafluorobutane.

In the step (2) (direct fluorination process), the 1,2,3,4-tetrachlorobutane prepared in the step (1) is allowed to react with a fluorine gas in the presence of a diluting gas in a gas phase, to prepare a mixture containing 1,2,3,4-tetrachlorohexafluorobutane. The diluting gas is preferably at least one selected from the group consisting of nitrogen, helium, argon, neon and hydrogen fluoride. In the present specification, nitrogen, helium, argon and neon are inclusively referred to inert gases. The mixture contain resulting 1,2,3,4-tetrachlorohexafluorobutane, resulting hydrogen fluoride, unreacted 1,2,3,4-tetrachlorobutane, unreacted fluorine gas, an intermediate of the reaction in the step (2) such as 1,2,3,4-tetrachlororotetrafluorobutane or 1,2,3,4-tetrachloropentafluorobutane, and the diluting gas. Moreover, the step (2) is preferably carried out in the absence of a catalyst.

The reaction in the step (2) is represented by the following formula (3).

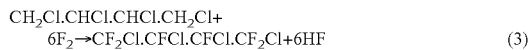
$$CH_2Cl.CHCl.CHCl.CH_2Cl + 6F_2 \rightarrow CF_2Cl.CFCl.CFCl.CF_2Cl + 6HF \quad (3)$$

In this step, since a fluorine gas having very high reactivity is used, the reaction of an organic compound, which is a substrate, with a fluorine gas occasionally causes explosion or corrosion. Furthermore, the reaction occasionally causes cut of carbon bonding or polymerization due to exothermic reaction, or side reactions such as rapid reaction or explosion due to carbon generation or deposition. The substitution of one C—H bond with C—F bond generates a heat of reaction of about −110 kcal/mol. As described above, the heat of reaction is in proportion to the mole number of a fluorine gas used, namely, the heat of reaction is larger in proportion with the increase of the fluorine gas amount. Therefore, the step easily causes cut of carbon bonding or explosion, and further causes a decline in the yield and thereby sometimes causes a problem in industrial production or operation.

On this account, in order to depress rapid generation of a heat of reaction in the direct fluorinating step, it is preferred to employ, for example, a method of diluting a fluorine gas with the above inert gas such as nitrogen or helium, and a method of diluting the organic compound, which is a substrate, also with the above inert gas or hydrogen fluoride. It is preferred to, further, employ a method of carrying out the reaction in a low temperature region and a method of carrying out the reaction in a gas phase by dividedly feeding a fluorine gas so as to contact the fluorine gas in limited amounts with the organic compound, which is a substrate.

In the step (2), into a reactor equipped with at least two feed openings, a mixed gas (A) of 1,2,3,4-tetrachlorobutane prepared in the step (3) or the step (5) and the diluting gas is fed from at least one feed opening and a mixed gas (B) of a fluorine gas and the diluting gas is fed from at least one of the other feed openings and thereby 1,2,3,4-tetrachlorobutane is allowed to react with a fluorine gas in the reactor, to prepare a mixture containing 1,2,3,4-tetrachlorohexafluorobutane. The concentration of 1,2,3,4-tetrachlorobutane is preferably 0.5 to 4 mol % based on the total amount of the mixed gases (A) and (B). When the organic compound, which is a substrate, is exposed to fluorine in a 1,2,3,4-tetrachlorobutane concentration of more than 4 mol %, burning or explosion will be occasionally taken place. The step (2), further, is a process of preparing a mixture containing 1,2,3,4-tetrachlorohexafluorobutane by, into a reactor having at least two feed openings, feeding a mixed gas (A) of 1,2,3,4-tetrachlorobutane prepared in the step (3) or the step (5) and the diluting gas from at least one feed opening and feeding a mixed gas (B) of a fluorine gas and the diluting gas from at least one of the other feed openings, thereby allowing 1,2,3,4-tetrachlorobutane to react with a fluorine gas in the reactor. The fluorine gas concentration is preferably 0.5 to 10 mol %, more preferably 0.5 to 6 mol % based on the total amount of the mixed gases (A) and (B). The diluting gas is preferably fed in a concentration of 86 to 99 mol % based on the total amount of the gases fed, to the reactor, namely the total amount of the gases (A) and (B).

The step (2) is preferably a process of preparing a mixture containing 1,2,3,4-tetrachlorohexafluorobutane by, into a reactor having at least three feed openings, feeding a mixed gas (A) of 1,2,3,4-tetrachlorobutane prepared in the step (3) or the step (5) and the diluting gas from at least one feed opening and feeding a mixed gas (B) of a fluorine gas and the diluting gas from at least two feed openings of the other feed openings, thereby allowing 1,2,3,4-tetrachlorobutane to react with a fluorine gas in the reactor. Furthermore, from the viewpoint of preventing the occurrence of burning or explosion, the step (2) is preferably a process of preparing a mixture containing 1,2,3,4-tetrachlorohexafluorobutane by, into a reactor having at least three feed openings, feeding a mixed gas (A) of 1,2,3,4-tetrachlorobutane prepared in the step (3) or the step (5) and the diluting gas from at least two feed openings and feeding a mixed gas (B) of a fluorine gas and the diluting gas from at least one of the other feed openings, thereby allowing 1,2,3,4-tetrachlorobutane to react with a fluorine gas in the reactor.

The step (2) is preferably a process of preparing a mixture containing 1,2,3,4-tetrachlorohexafluorobutane by allowing 1,2,3,4-tetrachlorobutane prepared in the step (3) or the step (5) to react with a fluorine gas at a pressure of from 0.05 to 1 MPa. Since the range where explosion will be occurred is generally wider in proportion with the pressure increase, the reaction is preferably carried put at a low pressure. In the step (2), the reaction of 1,2,3,4-tetrachlorobutane prepared in the step (3) or the step (5) with a fluorine gas is carried out at a temperature of preferably from 50 to 500° C., more preferably 150 to 450° C., thereby preparing a mixture containing 1,2,3,4-tetrachlorohexafluorobutane.

The material of the reactor is preferably a material having resistance to a corrosive gas, for example, an alloy containing nickel as an essential component, such as nickel, Inconel or Hastelloy.

After the step (2), at least one part of the mixture containing 1,2,3,4-tetrachlorohexafluorobutane may be taken out and liquid-liquid separated by, for example, cooling. That is to say, it may be separated into a hydrogen fluoride-rich phase and a 1,2,3,4-tetrachlorohexafluorobutane-rich phase. The hydrogen fluoride-rich phase contains hydrogen fluoride and further contains small amounts of organic substances such as an intermediate of the step (2), 1,2,3,4-tetrachlorohexafluorobutane and the like. The 1,2,3,4-tetrachlorohexafluorobutane-rich phase contains 1,2,3,4-tetrachlorohexafluorobutane and further contains hydrogen fluoride and a small amount of an intermediate of the step (2). The diluting gases (inert gases) other than hydrogen fluoride are removed by the liquid-liquid separation process. The hydrogen fluoride-rich phase, further, may be circulated as a diluting gas in the direct fluorinating process.

The production process of the present invention preferably comprises, further, a step (6) of allowing the resulting 1,2,3,4-tetrachlorohexafluorobutane-rich phase prepared by liquid-liquid separation of the mixture containing 1,2,3,4-tetrachlorohexafluorobutane prepared in the step (2), to contact with an alkali, thereby preparing crude 1,2,3,4-tetrachlorohexafluorobutane. In the step (6) (alkali contact process 1), the hydrogen fluoride contained in the 1,2,3,4-tetrachlorohexafluorobutane-rich phase is washed with, for example, an alkali aqueous solution.

Examples of the alkali aqueous solution may include sodium hydroxide aqueous solution, potassium hydroxide aqueous solution or the like. Moreover, the phase may be contacted with a purifying agent obtainable from an alkali metal compound, an alkaline earth metal compound, a carbonaceous solid material, alumina or zeolite. The hydrogen fluoride may be recovered in an aqueous state. The alkali contact process is preferably carried out at a temperature of from −10 to 70° C.

Since the crude 1,2,3,4-tetrachlorohexafluorobutane prepared through the alkali contact process contains moisture, it is preferably subjected to dehydration successively in a step (7) (dehydration process). That is to say, the production process of the present invention preferably comprises the step (6) of allowing the resulting 1,2,3,4-tetrachlorohexafluorobutane-rich phase prepared by liquid-liquid separating the mixture containing 1,2,3,4-tetrachlorohexafluorobutane prepared in the step (2), to contact with an alkali, thereby preparing crude 1,2,3,4-tetrachlorohexafluorobutane and the step (7) of dehydrating the crude 1,2,3,4-tetrachlorohexafluorobutane prepared in the step (6), thereby preparing crude dehydrated 1,2,3,4-tetrachlorohexafluorobutane. For the dehydration, it is preferred to use zeolite, for example, molecular sieves 3A, 4A or 5A.

At least one part of the crude dehydrated 1,2,3,4-tetrachlorohexafluorobutane prepared by the step (7) may be introduced into at least one distillation column by means of a pump or a compressor. In the distillation column, it is separated into the intermediate or the like and objective 1,2,3,4-tetrachlorohexafluorobutane. At least one part of the intermediate may be circulated in the step (2). That is to say, the production process of the present invention preferably comprises, further, a step (8) of feeding the crude 1,2,3,4-tetrachlorohexafluorobutane prepared by the step (7) into at least one distillation column, separating the intermediate prepared in the step (2) and feeding at least one part of the intermediate to the reactor. In the step, the intermediate and low boiling components such as nitrogen, oxygen, carbon monoxide or carbon dioxide are removed from the crude 1,2,3,4-tetrachlorohexafluorobutane prepared in the step (7). As a result, the crude 1,2,3,4-tetrachlorohexafluorobutane is purified to have a purity of preferably at least 95 mol %, more preferably at least 98 mol % and thereby recovered as a product (purified 1,2,3,4-tetrachlorohexafluorobutane product).

That is to say, the present invention is summarized as follows.

The process for producing the 1,2,3,4-tetrachlorohexafluorobutane according to the present invention comprises (1) chlorinating 1,3-butadiene, thereby preparing 1,2,3,4-tetrachlorobutane, and (2) allowing the 1,2,3,4-tetrachlorobutane prepared in the step (1) to react with a fluorine gas in the presence of a diluting gas in a gas phase, thereby preparing 1,2,3,4-tetrachlorohexafluorobutane.

In the step (2), the 1,2,3,4-tetrachlorobutane prepared in the step (1) is preferably allowed to react with a fluorine gas in the absence of a catalyst, thereby preparing 1,2,3,4-tetrachlorohexafluorobutane.

In the step (2) of preparing 1,2,3,4-tetrachlorohexafluorobutane, into the reactor having at least two feed openings, the mixed gas (A) of 1,2,3,4-tetrachlorobutane prepared in the step (3) or the step (5) and the diluting gas is fed from at least one feed opening and the mixed gas (B) of a fluorine gas and the diluting gas is fed from at least one of the other feed openings to allow the 1,2,3,4-tetrachlorobutane to react with a fluorine gas in the reactor. The concentration of 1,2,3,4-tetrachlorobutane is from 0.5 to 4 mol % based on the total amount of the mixed gases (A) and (B).

In the step (2) of preparing 1,2,3,4-tetrachlorohexafluorobutane, into the reactor having at least two feed openings, the mixed gas (A) of 1,2,3,4-tetrachlorobutane prepared in the step (3) or the step (5) and the diluting gas is fed from at least one feed opening and the mixed gas (B) of a fluorine gas and the diluting gas is fed from at least one of the other feed openings, to allow 1,2,3,4-tetrachlorobutane to react with a fluorine gas in the reactor. The concentration of a fluorine gas is from 0.5 to 10 mol % based on the total amount of the mixed gases (A) and (B). In the step (2), 1,2,3,4-tetrachlorohexafluorobutane is preferably prepared by allowing the 1,2,3,4-tetrachlorobutane prepared in the step (3) or the step (5) to react with a fluorine gas at a pressure of from 0.05 to 1 MPa.

In the step (2), 1,2,3,4-tetrachlorohexafluorobutane is preferably prepared by allowing the 1,2,3,4-tetrachlorobutane prepared in the step (3) or the step (5) to react with a fluorine gas at a temperature of from 50 to 500° C.

The process for producing 1,2,3,4-tetrachlorohexafluorobutane according to the present invention comprises (1) a step of chlorinating 1,3-butadiene, thereby preparing a mixture containing 1,2,3,4-tetrachlorobutane, and (2) a step of allowing the 1,2,3,4-tetrachlorobutane prepared in the step (1) to react with a fluorine gas in the presence of a diluting gas in a gas phase, thereby preparing a mixture containing 1,2,3,4-tetrachlorohexafluorobutane. The process, further, comprises (3) a step of separating 1,2,3,4-tetrachlorobutane from the mixture containing 1,2,3,4-tetrachlorobutane prepared in the step (1). The step (2) is characterized in that the 1,2,3,4- tetrachlorobutane prepared in the step (3) is allowed to react with a fluorine gas to prepare a mixture containing 1,2,3,4-tetrachlorohexafluorobutane.

The mixture containing 1,2,3,4-tetrachlorobutane contains 1,2,3,4-tetrachlorobutane and 3,4-dichlorobutene-1.

The production process of the present invention further comprises a step (4) of separating 3,4-dichlorobutene-1 from the mixture containing 1,2,3,4-tetrachlorobutane prepared in the step (1) and a step (5) of chlorinating 3,4-dichlorobutene-1 prepared in the step (4), thereby preparing 1,2,3,4-tetrachlorobutane. In the step (2), the 1,2,3,4-tetrachlorobutane prepared in the step (5) is allowed to react with a fluorine gas to prepare a mixture containing 1,2,3,4-tetrachlorohexafluorobutane.

The 1,2,3,4-tetrachlorobutane, further, is preferably a by-product.

Furthermore, the production process of the present invention preferably comprises a step (6) of liquid-liquid separating the mixture containing the 1,2,3,4-tetrachlorohexafluorobutane prepared in the step (2) and allowing a resulting 1,2,3,4-tetrachlorohexafluorobutane-rich phase to contact with an alkali, thereby preparing crude 1,2,3,4-tetrachlorohexafluorobutane (A), and a step (7) of dehydrating the crude 1,2,3,4-tetrachlorohexafluorobutane (A) prepared in the step (6), thereby preparing crude 1,2,3,4-tetrachlorohexafluorobutane (B).

In the step (6), the crude 1,2,3,4-tetrachlorohexafluorobutane (A) prepared by removing hydrogen fluoride from the 1,2,3,4-tetrachlorohexafluorobutane-rich phase contains water and an intermediate prepared in the reaction of the step (2). In the step (7), the crude 1,2,3,4-tetrachlorohexafluorobutane (B) prepared by removing water contains an intermediate prepared in the reaction of the step (2).

The production process of the present invention preferably comprises a step (8) of feeding the crude 1,2,3,4-tetrachlorohexafluorobutane (B) prepared in the step (7) into at least one distillation column, separating the intermediate obtained in the reaction of the step (2) and feeding at least one part of the intermediate to the reactor.

EXAMPLE

The present invention will be described with reference to the following examples. The present invention should not be limited with the examples.

Example 1

Step 1

1,3-Butadiene produced industrially was chlorinated to prepare dichlorobutene. In the chlorination, a mixture of 3,4-dichlorobutene-1 and 1,4-dichlorobutene-2 was produced. A part of the mixture was taken out, and then chlorinated and separated with distillation repeatedly to prepare 1,2,3,4-tetrachlorobutane. The resulting 1,2,3,4-tetrachlorobutane had a purity, as determined by gas chromatography, of 99.1 mol %.

Step 2

A reactor made of Inconel 600 having an inner diameter of 20.6 mmø and a length of 600 mm equipped with two gas feed openings (heating method with an electric heater) was previously subjected to passivation treatment by a fluorine gas at a temperature of 550° C. To the reactor, a nitrogen gas was passed through in an amount of 25 NL/h (total 50 NL/h) from the two gas feed openings and the reactor was heated to 250° C. Furthermore, hydrogen fluoride was passed through in an amount of 15 NL/h (total 30 NL/h) from each of the two gas feed openings. In this manner, a mixed gas of a nitrogen gas and hydrogen fluoride was used as a diluting gas.

Next, one of the diluting gas flow branched in an amount of 40 NL/h and the 1,2,3,4-terachlorobutane prepared in the step (1) in an amount of 1.0 NL/h were simultaneously fed to the reactor. Thereafter, the other diluting gas flow branched in an amount of 40 NL/h and a fluorine gas in an amount of 6.1 NL/h were simultaneously fed to the reactor and then the reaction was started.

The reaction results in the step (2) were evaluated in the following manner. After 3 hours from the reaction start, a reaction generated gas obtained from an outlet of the reactor (a mixture containing 1,2,3,4-tetrachlorohexafluorobutane prepared in the step (2)) was treated with potassium hydroxide and an aqueous solution of potassium iodide to remove hydrogen fluoride, unreacted fluorine gas and nitrogen gas which were contained in the reaction generated gas. Next, the mixture was extracted with an organic solvent and the composition of an extracting liquid was determined by gas chromatography. The results are shown below.

| | |
|---|---|
| 1,2,3,4-tetrachlorohexafluorobutane | 92.2% |
| Other components | 7.8% |

(unit: vol %)

Example 2

Step 1

1,3-Butadiene produced industrially was chlorinated to prepare dichlorobutene. In the chlorination, a mixture of 3,4-dichlorobutene-1 and 1,4-dichlorobutene-2 was produced. The 1,4 dichlorobutene-2 is isomerized to 3,4-dichlorobutene-1. In the step of producing chloroprene from 3,4-dichlorobutene-1 by dehydrochlorination, other chlorine compounds were separated with distillation as a by-product and then were made harmless and thrown away by burning treatment or the like.

The chlorine compounds produced as a by-product were separated and purified by a distillation column to prepare 1,2,3,4-tetrachlorobutane. The other by-products were made harmless by burning treatment. The resulting 1,2,3,4-tetrachlorobutane had a purity, determined by gas chromatography analysis, of 98.2 mol %.

Step (2)

A reactor made of Inconel 600 having an inner diameter of 20.6 mmø and a length of 1000 mm (heating method with an electric heater) was previously subjected to passivation treatment by a fluorine gas at a temperature of 550° C. To the reactor, a nitrogen gas was passed through in a total amount of 80 NL/h from the two gas feed openings provided in the column top and the reactor was heated to 300° C. In this manner, the nitrogen gas was used as a diluting gas.

Next, one of the diluting gas flow branched in an amount of 30 NL/h and the 1,2,3,4-terachlorobutane prepared in the step (1) in an amount of 2 NL/h were simultaneously fed to the reactor. Thereafter, the other diluting gas flow branched in an amount of 50 NL/h and a fluorine gas in an amount of 6.1 NL/h were simultaneously fed to the reactor and then the reaction was started.

Next, a nitrogen gas in an amount of 70 NL/h and a fluorine gas in an amount of 6 NL/h were fed from one gas feed opening provided on the center in the length wise direction of the reactor and the reaction was continued.

The reaction results in the step (2) were evaluated in the following manner. After 5 hours from the start of feeding the gas from the center of the reactor, a reaction generated gas (a mixture containing 1,2,3,4-tetrachlorohexafluorobutane prepared in the step (2)) was treated with potassium hydroxide and an aqueous solution of potassium iodide to remove hydrogen fluoride, unreacted fluorine gas and nitrogen gas which were contained in the reaction generated gas. Next, the mixture was extracted with an organic solvent and the composition of an extracting liquid was determined by gas chromatography. The results are shown below.

| 1,2,3,4-tetrachlorohexafluorobutane | 98.8% |
|---|---|
| Other components | 1.2% |

(unit: vol %)

After about 5 hours from the start of feeding the gas from the center of the reactor, a gas come out from the reactor outlet (a mixture containing 1,2,3,4-tetrachlorohexafluorobutane prepared in the step (2)) was collected with cooling and cooled to separate into a hydrogen fluoride-rich phase and a 1,2,3,4-tetrachlorohexafluorobutane-rich phase. In this separation, a nitrogen gas was also removed. The 1,2,3,4-tetrachlorohexafluorobutane-rich phase was extracted and washed with an alkali. Thereafter, the phase was subjected to dehydration treatment by molecular sieves to prepare crude 1,2,3,4-tetrachlorohexafluorobutane. Next, the crude 1,2,3,4-tetrachlorohexafluorobutane was purified with distillation to prepare a 1,2,3,4-tetrachlorohexafluorobutane purified product. The product was analyzed by gas chromatography. As a result, the product had a purity of 99.0 mol %.

Example 3

Step (1)

1,3-Butadiene produced industrially was chlorinated to produce 3,4-dichlorobutene-1 and 1,4-dichlorobutene-2 essentially. The 1,4 dichlorobutene-2 is isomerized to 3,4-dichlorobutene-1. The reaction mixture was subjected to separation with distillation to prepare 3,4-dichlorobutene-1. The 3,4-dichlorobutene-1 had a purity, as determined in gas chromatography, of 99.3 mol %.

To a 200 mL internal volume four neck glass flask, 50.14 g (401.1 mmol) of 3,4-dichlorobutene-1 was fed and the reaction temperature was kept at 40° C. with a hot bath while stirring the 3,4-dichlorobutene-1.

The reaction was started while feeding a nitrogen gas in an amount of 5 mL/min and a chlorine gas in an amount of 88.8 mL/min from gas feed openings. After about 103 min from the reaction start, a chlorine gas was fed in an amount of 8 mL/min and the reaction was further continued for about 30 min and thereafter, the feed of a chlorine gas was stopped to complete the reaction. The total amount of the chlorine gas fed was 419 mmol.

The reaction liquid was collected and analyzed by gas chromatography. The results are shown below.

| 1,2,3,4-tetrachlorobutane | 94.3 mol % |
|---|---|
| unreacted 3,4-dichlorobutene-1 | 2.7 mol % |
| Other components | 3.0 mol % |

With regard to the isomers in the 1,2,3,4-tetrachlorobutane, the proportion of dl form to meso form was 45.3/54.7.

Step 2

A reactor made of Inconel 600 having an inner diameter of 20.6 mmø and a length of 600 mm equipped with two gas feed openings (heating method with an electric heater) was previously subjected to passivation treatment by a fluorine gas at a temperature of 550° C. To the reactor, a nitrogen gas was passed through in an amount of 40 NL/h (total 80 NL/h) from the two gas feed openings and the reactor was heated to 250° C.

Next, one of the diluting gas flow branched in an amount of 40 NL/h and the 1,2,3,4-terachlorobutane prepared in the step (1) in an amount of 1.0 NL/h were simultaneously fed to the reactor. Thereafter, the other diluting gas flow branched in an amount of 40 NL/h and a fluorine gas in an amount of 6.1 NL/h were simultaneously fed to the reactor and then the reaction was started.

The reaction results in the step (2) were evaluated in the following manner. After 3 hours from the reaction start, a reaction generated gas obtained from the reactor outlet (a mixture containing 1,2,3,4-tetrachlorohexafluorobutane prepared in the step (2)) was treated with potassium hydroxide and an aqueous solution of potassium iodide to remove hydrogen fluoride, unreacted fluorine gas and nitrogen gas which were contained in the reaction generated gas. Next, the mixture was extracted with an organic solvent and the composition of an extracting liquid was determined by gas chromatography. The results were as follows.

| 1,2,3,4-tetrachlorohexafluorobutane | 91.8% |
|---|---|
| Other components | 8.2% |

(unit: vol %)

The invention claimed is:

1. A process for producing 1,2,3,4-tetrachlorohexafluorobutane which process comprises:
(1) a step of chlorinating 1,3-butadiene, thereby preparing a mixture containing 1,2,3,4-tetrachlorobutane, and
(2) a step of allowing the 1,2,3,4-tetrachlorobutane prepared in the step (1) to react with a fluorine gas in the presence of a diluting gas in a gas phase, thereby preparing a mixture containing 1,2,3,4-tetrachlorohexafluorobutane.

2. The process for producing 1,2,3,4-tetrachlorohexafluorobutane according to claim 1 wherein the step (2) comprises allowing the 1,2,3,4-tetrachlorobutane prepared in the step (1) to react with a fluorine gas in the absence of a catalyst, thereby preparing a mixture containing 1,2,3,4-tetrachlorohexafluorobutane.

3. The process for producing 1,2,3,4-tetrachlorohexafluorobutane according to claim 1 wherein the step (1) comprises chlorinating 1,3-butadiene, thereby preparing a mixture containing 1,2,3,4-tetrachlorobutane and 3,4-dichlorobutene-1.

4. The process for producing 1,2,3,4-tetrachlorohexafluorobutane according to claim 3 wherein the 1,2,3,4-tetrachlorobutane is a by-product.

5. The process for producing 1,2,3,4-tetrachlorohexafluorobutane according to claim 1 which process further comprises:
(3) a step of separating 1,2,3,4-tetrachlorobutane from the mixture containing 1,2,3,4-tetrachlorobutane prepared in the step (1),
wherein the step (2) comprises allowing the 1,2,3,4-tetrachlorobutane prepared in the step (3) to react with a fluorine gas thereby preparing a mixture containing 1,2,3,4-tetrachlorohexafluorobutane.

6. The process for producing 1,2,3,4-tetrachlorohexafluorobutane according to claim 1 which process further comprises:
(4) a step of separating 3,4-dichlorobutene-1 from the mixture containing 1,2,3,4-tetrachlorobutane prepared in the step (1) and
(5) a step of chlorinating the 3,4 dichlorobutene-1 prepared in the step (4), thereby preparing 1,2,3,4-tetrachlorobutane,
wherein the step (2) comprises allowing the 1,2,3,4-tetrachlorobutane prepared in the step (5) to react with a fluorine gas, thereby preparing a mixture containing 1,2,3,4-tetrachlorohexafluorobutane.

7. The process for producing 1,2,3,4-tetrachlorohexafluorobutane according to claim 1 wherein the diluting gas is at least one gas selected from the group consisting of nitrogen, helium, argon, neon and hydrogen fluoride.

8. The process for producing 1,2,3,4-tetrachlorohexafluorobutane according to claim 5 or 6 wherein the step (2) comprises allowing 1,2,3,4-tetrachlorobutane to react with a fluorine gas in a reactor having at least two feed openings by feeding a mixed gas (A) of 1,2,3,4-tetrachlorobutane prepared in the step (3) or (5) and the diluting gas from at least one feed opening and feeding a mixed gas (B) of a fluorine gas and the diluting gas from at least one of the other openings, thereby preparing a mixture containing 1,2,3,4-tetrachlorohexafluorobutane, and the concentration of 1,2,3,4-tetrachlorobutane is from 0.5 to 4% by mole based on the total amount of the mixed gases (A) and (B).

9. The process for producing 1,2,3,4-tetrachlorohexafluorobutane according to claim 5 or 6 wherein the step (2) comprises allowing 1,2,3,4-tetrachlorobutane to react with a fluorine gas in a reactor having at least two feed openings by feeding a mixed gas (A) of 1,2,3,4-tetrachlorobutane prepared in the step (3) or (5) and the diluting gas from at least one feed opening and feeding a mixed gas (B) of a fluorine gas and the diluting gas from at least one of the other openings, thereby preparing a mixture containing 1,2,3,4-tetrachlorohexafluorobutane, and the concentration of a fluorine gas is from 0.5 to 10% by mole based on the total amount of the mixed gases (A) and (B).

10. The process for producing 1,2,3,4-tetrachlorohexafluorobutane according to claim 5 or 6 wherein the step (2) comprises allowing the 1,2,3,4-tetrachlorobutane prepared in the step (3) or (5) to react with a fluorine gas at a pressure of from 0.05 to 1 MPa, thereby preparing a mixture containing 1,2,3,4-tetrachlorohexafluorobutane.

11. The process for producing 1,2,3,4-tetrachlorohexafluorobutane according to claim 5 or 6 wherein the step (2) comprises allowing the 1,2,3,4-tetrachlorobutane prepared in the step (3) or (5) to react with a fluorine gas at a temperature of from 50 to 500° C., thereby preparing a mixture containing 1,2,3,4-tetrachlorohexafluorobutane.

12. The process for producing 1,2,3,4-tetrachlorohexafluorobutane according to claim 8 which process further comprises:
(6) a step of liquid-liquid separating the mixture containing 1,2,3,4-tetrachlorohexafluorobutane prepared in the step (2) and allowing a resulting 1,2,3,4-tetrachlorohexafluorobutane-rich phase to contact with an alkali, thereby preparing crude 1,2,3,4-tetrachlorohexafluorobutane, and
(7) a step of dehydrating the crude 1,2,3,4-tetrachlorohexafluorobutane prepared in the step (6), thereby preparing crude 1,2,3,4-tetrachlorohexafluorobutane.

13. The process for producing 1,2,3,4-tetrachlorohexafluorobutane according to claim 9 which process further comprises:
(6) a step of liquid-liquid separating the mixture containing 1,2,3,4-tetrachlorohexafluorobutane prepared in the step (2) and allowing a resulting 1,2,3,4-tetrachlorohexafluorobutane-rich phase to contact with an alkali, thereby preparing crude 1,2,3,4-tetrachlorohexafluorobutane, and
(7) a step of dehydrating the crude 1,2,3,4-tetrachlorohexafluorobutane prepared in the step (6), thereby preparing crude 1,2,3,4-tetrachlorohexafluorobutane.

14. The process for producing 1,2,3,4-tetrachlorohexafluorobutane according to claim 12 or 13 which further comprises (8) a step of feeding the crude 1,2,3,4-tetrachlorohexafluorobutane prepared in the step (7), to at least one distillation column, separating an intermediate in the reaction of step (2) and feeding at least a part of the intermediate to the reactor.

* * * * *